United States Patent [19]
Keusch et al.

[11] Patent Number: 5,225,236
[45] Date of Patent: Jul. 6, 1993

[54] COMPOSITE PROTECTIVE DRAPES

[76] Inventors: Preston Keusch, 220 E. 84th St., Apt. 3-D, New York, N.Y. 10028; Christine A. Czap, 197 Oriole Dr., Montgomery, N.Y. 12549; Keith A. Murdock, 288 Haverstraw Rd., Suffern, N.Y. 10901

[21] Appl. No.: 450,657

[22] Filed: Dec. 14, 1989

Related U.S. Application Data

[63] Continuation-in-part of Ser. No. 373,412, Jun. 28, 1989, abandoned.

[51] Int. Cl.$^5$ .................. A61B 19/08; B32B 15/08; B32B 33/00
[52] U.S. Cl. ........................... 428/77; 128/362; 128/849; 428/221; 428/242; 428/246; 428/247; 428/285; 428/316.6; 428/318.4; 428/319.1; 428/319.3; 428/319.9; 428/321.1; 428/920; 606/2
[58] Field of Search .............. 606/2; 128/849, 362; 428/319.1, 77, 221, 242, 246, 247, 316.6, 318.4, 319.3, 319.9, 321.1, 920

[56] References Cited

U.S. PATENT DOCUMENTS

| | | |
|---|---|---|
| Re. 27,401 | 6/1972 | Wichterle et al. . |
| 3,220,960 | 11/1965 | Wichterle et al. . |
| 3,264,202 | 8/1966 | King . |
| 3,419,006 | 12/1968 | King . |
| 3,629,170 | 12/1971 | Yamanouchi et al. . |
| 3,781,381 | 12/1973 | Koleske et al. . |
| 3,898,143 | 8/1975 | Assarsson et al. . |
| 3,993,551 | 11/1976 | Assarsson et al. . |
| 3,993,552 | 11/1976 | Assarsson et al. . |
| 3,993,553 | 11/1976 | Assarsson et al. . |
| 3,998,215 | 12/1976 | Anderson et al. . |
| 4,387,187 | 6/1983 | Newton . |
| 4,520,814 | 6/1985 | Weeks ........................ 606/2 |
| 4,558,093 | 12/1985 | Hatzenbuhler ............... 128/849 |
| 4,596,858 | 6/1986 | Gregor et al. . |
| 4,601,286 | 7/1986 | Kaufman ..................... 128/894 |
| 4,603,076 | 7/1986 | Bowditch .................... 428/319.1 |
| 4,616,641 | 10/1986 | Teeple ......................... 606/2 |
| 4,684,558 | 8/1987 | Keusch et al. . |
| 4,699,146 | 10/1987 | Sieverding . |
| 4,705,753 | 11/1987 | Gregor et al. . |
| 4,706,680 | 11/1987 | Keusch et al. . |
| 4,715,366 | 12/1987 | Teeple ......................... 606/2 |
| 4,746,514 | 5/1988 | Warner . |
| 4,750,482 | 6/1988 | Sieverding . |
| 4,901,738 | 2/1990 | Brink et al. ................. 606/2 |

FOREIGN PATENT DOCUMENTS 247797 12/1987 European Pat. Off. ............ 128/849
WO88/02622 4/1988 World Int. Prop. O. .

OTHER PUBLICATIONS

Bauman, N. "Laser Drape Fires: How Much of a Risk?" Laser Medicine & Surgery News and Advances, Aug. 1989.
Turut, P. et al., Bull. Soc. Opht. France 1988, 5, LXXXVIII.
Sosis, M. B., Anesth. Analg. 1989, 68, 392-3.
Gregor et al., J. Applied Polymer Sci. 1985, 30, 1113-1132.

*Primary Examiner*—James C. Cannon

[57] ABSTRACT

The present invention describes a protective drape and methods for using the drape to protect or shield an object against the harmful effects of accidental exposure to optical radiation, electrical discharge, heat, or an open flame. The present invention comprises a flexible solid sheet and a composite scrim and includes methods for predicting/determining the suitability of a chosen metallic component for use in the instant drape.

56 Claims, 4 Drawing Sheets

COMPOSITE PROTECTIVE DRAPES

This application is a continuation-in-part of copending application Ser. No. 07/373,412, filed on Jun. 28, 1989, and now abandoned, which is incorporated by reference herein in its entirety.

TABLE OF CONTENTS

1. Background of the Invention
2. Summary of the Invention
3. Brief Description of the Figures
4. Detailed Description of the Invention
   4.1. Hydrogels Useful in the Invention
   4.2. Polymer Foams
   4.3. The Composite Scrim
   4.4. Novel Hydrogels with Liquid Aqueous Interiors (Aquagels)
   4.5. Electroconductive Protective Drapes
   4.6. Method for Determining Burn-Through Times
   4.7. Method for Determining Suitability of a Particular Metallic Component
5. Examples
   5.1. Protective Drape Having a Hydrogel with Tacky and Adhesive Properties
   5.2. Protective Drape Having a Hydrogel with Tacky and Adhesive Properties, Enhanced Laser Scattering, and Extended Shelf Life
   5.3. Sterile Protective Drape Having a Hydrogel with Non-Stringy Properties, Enhanced Laser Scattering, and Extended Shelf Life
   5.4. Protective Drape Having a Hydrogel with Increased Water Content
   5.5. Protective Drape Having a Hydrogel with Thick Aluminum Tri-Laminate Scrim
   5.6. Protective Drape Employing a Thick Copper Tri-Laminate Scrim
   5.7. Protective Drape Employing a Polypropylene Scrim
   5.8. Sterile Adhesive Protective Drape Employing An Aqueous Solution of Poly(vinyl Pyrrolidone) (PVP)
   5.9. Protective Drape Employing an Aqueous Solution Containing a Blend of Poly(vinyl Pyrrolidone) (PVP) and Poly(ethylene Oxide) (PEO)
   5.10. Conductive Protective Drape Having a Hydrogel with Tacky and Adhesive Properties, and Extended Shelf Life
   5.11. Protective Drape Having a Liquid Center
   5.12. Decreased Flashback with Metallic Meshes on Top of Copper Scrim
   5.13. Double Foil to Give Added Protection After Initial Burn-Through
   5.14. Nonflammability of Protective Drapes

1. BACKGROUND OF THE INVENTION

The many advantages offered by laser surgery has made the technique very popular in surgical procedures spanning the different branches of medicine. Some estimates have indicated that as many as 1 million surgical procedures are performed each year which involve the use of lasers at some stage. Of this number, approximately half are performed endoscopically, and the remainder can be classified as "open" laser surgery. The latter category suffers from a much greater incidence and probability of inadvertent exposure to powerful and destructive laser light. Practically all the objects in the operating room, including medical equipment and personnel, are potential accidental targets of a direct or reflected beam.

The outcome of accidental exposure to both focused and unfocused laser light includes burns to human tissues, damage to equipment, ignition of combustible materials including ordinary fabrics and any flammable materials. The danger from fires started by unfocused laser light is particularly acute.

For example, a recent communication by Turut, P. et al. in *Bull. Soc. Opht. France* 1988, 5, LXXXVIII chronicles the results of mistakes made by careless operators of laser equipment: lens burns with argon laser, corneal burns in laser iridotomy, intraocular lens marks after YAG posterior capsulotomy, retinal burns with YAG laser, and other serious complications. Rather dramatic fires and even explosions have been reported in the combustion of endotracheal tubes upon exposure to $CO_2$ laser light (See, for example, Sosis, M. B. in *Anesth. Analg.* 1989, 68, 392-3 in which the author reports the results of attempts to protect endotracheal tubes with metallic tape). Another article specifically referring to laser drape fires is by Bauman, N., "Laser Drape Fires: How Much of a Risk?", *Laser Medicine & Surgery News and Advances*, August 1989.

It is apparent that conventional surgical drapes made of cellulose or other combustible materials, including synthetic polymers, offer little protection and, in fact, constitute a fire hazard in an operating room in which lasers are in use. Frequently, the medical practitioner has even resorted to using towels soaked in saline in an effort to obtain better protection than a dry cloth drape. Besides being hygienically unsuitable, such towels have been known to dry out during the medical procedure and ignite upon accidental exposure to the laser. Other means of protection which purportedly shield healthy tissue or equipment from the harmful beams are known and have taken the form of barriers or laser drapes. A metallic blanket comprising a polymeric inner sheet completely enclosed by aluminum foil is described in U.S. Pat. No. 4,715,366 issued to Teeple. Cotton gauze, woven textile fabrics, and elastomeric materials such as a pliable polyolefin are recited as possible examples of inner sheets. It is specified that the inner sheets remain moldable or drapable while being resistant to melting or ignition. While such a metallic blanket may possibly be effective in preventing the immediate penetration of a laser beam (no experimental data are provided), such a metallic blanket most certainly lacks the ability to adequately and quickly disperse away from tissue the large concentration of heat generated at the vicinity of the incident beam. In addition, the possibility that the inner materials may ignite remains, or worse, areas of the sheet may become so hot as to burn the tissue sought to be protected underneath the metallic blanket. It is crucial to note that many patients would be under general anesthesia and would be unable to feel, much less communicate, any discomfort. Moreover, a reflective exterior surface such as that provided by an aluminum foil exterior, may exacerbate the danger arising from reflected or deflected beams.

Another means for protecting healthy tissue from stray laser light which utilizes a conventional hydrogel as the surgical drape material, is disclosed in U.S. Pat. No. 4,601,286 issued to Kaufman. A specific embodiment recited in this reference includes a metallic sheet interposed between two layers of hydrogel material. It is apparent from the disclosures of this reference that any protection accorded by these laser shields applies only to a CO₂ laser operated at low power (15 watts), if that. Although one might expect an embodiment having a metallic sheet interposed between two layers of hydrogel to perform better than layers of plain hydrogel, such expectation does not necessarily hold. It has been found, in fact, that the metallic sheet, such as an aluminum foil, which is present within the hydrogel bursts outward towards the source of the laser light, presumably, because of the pressure exerted by the gases building up underneath the metallic sheet upon extended exposure of the shield to a focused stationary beam. Having suffered a loss in its integrity, the metallic sheet is no longer able to provide any protection. Furthermore, the behavior of these laser shields when the CO₂ laser is operated at higher intensity or when shorter wavelength (higher energy) lasers are used is quite suspect. Moreover, the bare sheet of aluminum foil tends to become crinkled or torn, especially during processing, separating from the hydrogel sheet and eventually corroding from the effects of air and moisture. Indeed, these prior art materials have very poor shelf lives with the metal rapidly corroding and initiating the degradation of the hydrogel itself. Corroded materials are, of course, unsuitable for use in any hospital environment.

Of equal significance, the reflective nature of the facing surface produces a glare under the high intensity lamps of an operating room making it difficult for surgeons and nurses to operate. Other deficiencies of these laser shields include their failure to alleviate the concern for stray laser light reflected off of the shiny metallic surface of the bare foil. The possibility that water or other aqueous solutions may need to be added to the laser shield dressing, especially where wet towels are also used, to replace water lost during the surgical procedure, also adds yet another item to be considered and monitored by the already highly stressed and burdened surgical team. Lastly, this reference fails to recognize, much less address, the danger associated with the ignition of combustible materials due to direct exposure to focused or unfocused laser light.

A laser-resistant back-up pad is described in U.S. Pat. No. 4,520,814. This pad which is meant to be inserted between layers of incised tissues and is comprised of an elastomeric, rubber substrate over which is bonded a coating of a mixture of elastomer and a metal powder. A wet gauze is preferably placed over the resulting pad. The laser reflective coating described is initially a solution which is applied separately and needs to be dried and/or cured, preferably baked.

Thus, a need for a protective drape which is conformable, capable of withstanding incident laser light of varying wavelengths at high power settings, capable of adequately dispersing the heat generated by the incident beam, which is easily processable, and one which has stable long-term storage characteristics remains unfulfilled. Furthermore, such a protective drape must eliminate or greatly reduce the possibility of stray laser light reflecting off of the protective drape and inadvertently causing harm or injury to adjacent objects or tissue. Most importantly, such a drape must provide adequate protection for a significant length of time without suffering catastrophic failure such as the bursting phenomenon observed with existing laser drapes. Additionally, the outward facing surface of an ideal drape should be substantially non-reflective. It is also most desirable that a protective drape be found which has all the characteristics enumerated above and also be readily sterilizable for use in an aseptic environment and, furthermore, have the versatility to accommodate various additives.

2. SUMMARY OF THE INVENTION

The present invention provides a protective drape which in one embodiment is comprised of at least one sheet of a viscoelastic hydrophilic gel in which is incorporated at least one composite scrim, comprising a reflective, non-radiant-energy-absorbing metallic component and a water-insoluble polymeric substance. In another embodiment, the hydrophilic gel of the protective drape is replaced by a polymer foam which may be hydrophobic or hydrophilic in nature. With hydrophobic foams, the porous internal and external structure should comprise open, interconnected voids. In the case of hydrophilic foams, the cells may be fully enclosed or open. Thus, a water-saturated hydrophilic foam can be considered a "hydrogel." In addition, the surface of a hydrophobic foam may be modified to become water-wettable.

Any hydrogel having a water content of at least about 80 weight percent may be used in the instant protective drape, preferably over about 90 weight percent water, and most preferably is derived from an irradiation crosslinkable polymer, such as poly(ethylene oxide). The composite scrim may be prepared in a heterogeneous or homogeneous configuration such as a scrim comprised of discrete layers of components in particular a metallic foil laminated with one or more layers of a polymeric film, or a flexible polymeric sheet in which is imbedded finely divided metallic particles, respectively. Alternatively, the composite scrim may be of a porous configuration or a dense fibrous mesh. Such a latter configuration has the added advantage of dispersing the incident beam within the internal structures of the porous or fibrous network. Thus, the composite scrim is meant to encompass any contiguous material, be it in a form of a solid sheet, thin film, or porous layer, which material is used to reinforce the bulk of the drape and which aids in deflecting and/or dissipating the harmful energy of an incident laser light away from the burn site.

In the case of metallic sheets or foils, the surface of the metallic component preferably has a matte finish. The composite scrim may also be composed of multiple layers of metallic foils or sheets joined together by a high-temperature, thermally nonconductive adhesive.

In any of a number of configurations, the protective drape of the present invention offers superior protection against damage or injury arising from exposure to high intensity optical radiation, such as laser light of various wavelengths. The protective drape is quite versatile being able to accommodate a variety of additives and may also comprise additional layers of backing material. If desired, the protective drape may be sterilized for use in an aseptic environment.

In a particular embodiment of the present invention, a protective drape is disclosed which comprises:

(a) at least one flexible solid sheet of a viscoelastic hydrophilic gel comprising a homogeneous mixture of at least about 80% by weight water and a substantially water-insoluble, water-swellable, hydrophilic polymer; and (b) at least one flexible composite scrim comprising a laminate of at least one foil or sheet of a metallic component and at least one film of a hydrophobic polymeric substrate, said scrim being in intimate contact with said flexible solid sheet and which metallic component has a sufficient degree of reflectivity, thermal conductivity, and thickness, to provide a protective drape having top and bottom external surfaces, which drape is capable of effectively dissipating an accidentally directed beam of laser light.

In another embodiment of the present invention, the protective drape comprises at least one flexible solid sheet comprising a porous polymer foam and at least one flexible composite scrim in intimate contact with said foam.

The present invention also provides a method for protecting or shielding an object from harmful optical radiation, stray sparks from an electrosurgical scalpel, sources of intense heat, or even an open flame, which method comprises covering at least part of the object sought to be protected with the instant protective drape. The conformable protective drape of the present invention may be arranged over flat or uneven surfaces. Several drapes may also be arranged in any desired manner to provide a suitable operating arena. In particular a method is described for shielding an object from harmful optical radiation, electrical discharge, heat, or flame and said object, said protective drape being in intimate contact with said object and which drape comprises:

(a) at least one flexible solid sheet of a viscoelastic hydrophilic gel comprising a homogeneous mixture of at least about 80% by weight water and a substantially water-insoluble, water-swellable, hydrophilic polymer; and (b) at least one flexible composite scrim comprising a laminate of at least one foil or sheet of a metallic component and at least one film of a hydrophobic polymeric substrate, said scrim being in intimate contact with said flexible solid sheet and which metallic component has a sufficient degree of reflectivity, thermal conductivity, and thickness.

In another aspect of the present invention a method is provided for retarding the ignition of combustible materials, such as a hospital surgical gown, arising from exposure to focused or unfocused laser light, which method comprises interposing at least one flexible solid sheet of a viscoelastic hydrophilic gel between the source of said nonfocused layer light and said combustible material, said flexible solid sheet being in intimate contact with said combustible material and said viscoelastic hydrophilic gel comprising a mixture of at least about 80–85% by weight water and a substantially water-insoluble, water-swellable, hydrophilic polymer.

Other aspects and objectives of this invention will become apparent from the descriptions and examples that follow.

3. BRIEF DESCRIPTION OF THE FIGURES

FIG. 5 shows the set-up for the burn-through experiments described herein in which test platforms (7) hold the test hydrogel drape (9) and heat-sensitive material (8), respectively. A performing protective drape is illustrated in FIG. 5A. The top platform has an opening (10) which allows the passage of laser light which has "burned-through" the failed test drape as illustrated in FIG. 5B. The particular embodiments of the present invention which were tested demonstrated superior protection against exposure to $CO_2$ laser light under the test conditions enumerated in Section 4.6.

FIGS. 6A and 6B illustrate the geometry for a model for the dissipation of laser light in which the top view (6A) indicates the relationship between R, (the radius of the laser column), $\Delta r$, and L (the thickness of the metallic component), as discussed in Section 4.7.

4. DETAILED DESCRIPTION OF THE INVENTION

The protective drape of the instant invention is comprised of an aqueous swellable material particularly a hydrogel material and a composite scrim. Hydrogel materials which are known in the art, as well as a novel material which is described herein, can be used in the present invention. Furthermore, various additives which perform different functions may be incorporated in these hydrogels, and additional layers of backing material may be included as well. These protective drapes provide superior shielding properties as evidenced by the results of burn-through experiments using a carbon dioxide laser operating at high power density levels. In addition, the present drapes provide superior storage stability (no detectable deterioration after at least six months) relative to a hydrogel sheet with a bare metal foil.

4.1. HYDROGELS USEFUL IN THE INVENTION

Many viscoelastic hydrogels described in the art are suitable for use in this invention. The primary requirement is that the hydrogels be comprised of water to a high extent, at least about 80% by weight and preferably over about 90% by weight. The upper limit is generally dictated by the nature of the hydrophilic material which gives the hydrogel its viscoelastic or reversibly deformable, high-water-content, solid properties. Typically, the hydrophilic material should comprise at least about 2% by weight of the total to give a hydrogel that has sufficient cohesive strength and one which does not come apart readily. The hydrophilic material of said hydrogels is commonly a substantially water-insoluble, water-swellable polymer having hydrophilic functional groups derived from heteroatoms with at least one lone pair of electrons capable of forming a hydrogen bond. Polymers such as polyacrylamide, hydrolyzed or partially hydrolyzed acrylonitrile, hydroxy-modified celluloses, their copolymers, and the like form useful hydrogels. Water-soluble polymers form excellent hydrogels upon crosslinking of the polymer chains. Suitable crosslinkable water-soluble polymers include, but are not limited to, poly(ethylene oxide), poly(vinyl alcohol), poly(vinyl pyrrolidone), poly(ethylene imine), mixtures, blends, or copolymers thereof. Furthermore a variety of synthetic and naturally-occurring materials may be incorporated in the hydrogel formulations including carbohydrates, polysaccharides (See, for example, U.S. Pat. No. 4,746,514), polysaccharic acid, proteinaceous substances like collagen or gelatin (as described, for example, in WO 88/02622), pigments, refractive particles, stabilizers, bacteriocides, fungicides, electrolytes, metallic particles, oxides, fire retardants and other purposeful additives so long as they do not adversely affect the integrity and long-term stability of the hydrogel.

Methods for the production of suitable hydrogels may be found in U.S. Pat. Nos. 3,264,202 and 3,419,006, in which aqueous solutions of poly(ethylene oxide) are exposed to high energy radiation to form solid crosslinked gel-like materials. In general, alpha particles, beta particles, gamma rays, X-rays, electron beams, or high energy ultraviolet radiation may be used effectively to precipitate the crosslinking of the polymer chains. In fact, aqueous solutions of essentially linear mixtures of poly(ethylene oxide) and other water-soluble polymers are crosslinked readily as described in a series of U.S. Patents issued to Assarsson and King: U.S. Pat. No. 3,898,143 (PEO and starch); U.S. Pat. No. 3,993,551 (PEO and polyacrylic acids, polyacrylates, anhydride copolymers, and the like); U.S. Pat. No. 3,993,552 (PEO and gelatin); and U.S. Pat. No. 3,993,553 (PEO and cellulose derivatives). Additional hydrogels are disclosed in U.S. Pat. No. 3,220,960 and Reissue U.S. Pat. No. 27,401. Potentially useful materials are likewise described in U.S. Pat. Nos. 4,699,146 and 4,750,482 both issued to Sieverding. The Sieverding patents also contain an extensive list of sources of high energy radiation such as cyclotrons, linear accelerators, spent nuclear fuel, radioactive isotopes, X-ray equipment, Van de Graf generators, or electron accelerators.

Crosslinking of the initially water-soluble polymer chains may also be accomplished by the addition of chemical crosslinking agents. These gelling agents are preferably compounds which decompose into free radicals or produce species which are able to initiate a free radical reaction sequence. The decomposition of these agents is preferably thermally or photochemically initiated, and the reactions which subsequently take place eventually lead to the crosslinking of the polymer chains into a water-insoluble but hydrophilic polymer network. Examples of suitable crosslinking agents include, but are not limited to, ethylene glycol dimethacrylate, and others apparent to one skilled in the art. Suitable initiators include, but are not limited to azonitriles, such as azobis(isobutyronitrile); aliphatic and aromatic peroxides such as m-chloroperbenzoic acid and benzoyl peroxide; hydroperoxides; and alkali metal perborates. Suitable experimental procedures for the use of sodium or potassium perborates are described in U.S. Pat. No. 3,998,215 issued to Anderson and Gumbusky. Other reagents for crosslinking polymer claims may be envisioned depending upon the functional groups present on the polymer backbone. For example, polycarboxylates may be useful in linking poly(vinyl alcohol) chains; polyols and polyamines may form bridging moieties between polymer chains having pendant carboxyl or other electrophilic functional groups. The degree of crosslinking must be sufficiently high, however, to produce a substantially water-insoluble, water-swellable, hydrophilic polymer network and a stable gel. A procedure in which a hydrophilic monomer is copolymerized with a sufficient amount of a crosslinking agent is described in U.S. Pat. No. 3,220,960. Conditions are also disclosed for producing transparent or microporous materials.

Particularly useful hydrogels are described in U.S. Pat. No. 4,684,558. These hydrophilic irradiation crosslinked poly(ethylene oxide) gels have the additional properties of tackiness and adhesiveness. Thus, in a particularly embodiment of the present invention, protective drapes manufactured from adhesive hydrogels have sticky, but cohesive, external surfaces and may be applied directly to the surface of equipment, to the patient's skin, or to the surfaces of most objects not necessarily limited to an operating room setting without the need for applying separate adhesive substances or tape. In addition a method for producing electrically conductive adhesive hydrogel sheets is disclosed in U.S. Pat. No. 4,706,680. The protective drapes of the present invention may incorporate sections in which the hydrogel is electrically conductive, especially when such drapes are used to protect the chest area of patients in an operating room (more in Section 4.5, infra) or when electrodes are to be attached to spots of the patient's body for monitoring bodily functions or reactions.

Certain particles or pigments, when incorporated into the hydrogel formulation, may give rise to a protective drape with improved characteristics. For instance, hydrogel sheets which contain small amounts of titanium dioxide provide protective drapes which attenuate optical glare, and may even be able to withstand the effects of a focused laser beam for longer periods of time, relative to drapes made from hydrogels having no titanium dioxide. Other refractive particles, pigments, or fire retardants which may be incorporated into the hydrogel include, but are not limited to, zirconium dioxide, silicon dioxide, aluminum oxide, molybdenum oxide, zinc oxide, or mixtures thereof. Particulates, such as small metal particles, and pigments may also be useful for the dispersion or absorption of selected wavelengths of laser light.

4.2. POLYMER FOAMS

The protective drape of the present invention may also comprise at least one flexible solid sheet comprising a porous polymer foam and at least one flexible composite scrim in intimate contact with said foam. The foam is prepared from a polymeric material which is preferably crosslinked. Both hydrophobic and hydrophilic polymers may be used, but the cells or voids of a hydrophobic polymer foam should be open and substantially interconnected to allow for the permeation and entrapment of water. In addition, the surface of a hydrophobic foam may also be modified to be water-wettable. Methods for modifying or derivatizing polymer surfaces are well known. One method involves introducing a comonomer bearing desirable hydrophilic functional groups to the monomer precursor of the primary hydrophobic polymer. (See, for example, the work of Gregor et al. in *J. Applied Polymer Sci.* 1985, 30, 1113-1132 and U.S. Pat. No. 4,705,753, the complete disclosures of which references, including those mentioned below, are incorporated by reference herein). Another method involves blending a water-wettable polymer with a bulk polymer. Such blending techniques are described, for example, in U.S. Pat. Nos. 3,629,170; 3,781,381; and 4,387,187. A variation involving an additional crosslinking step is disclosed in U.S. Pat. No. 4,596,858. Yet other methods are readily apparent to those skilled in the art.

Materials useful for the preparation of porous polymer foams, as well as the methods for their preparation, are well-known. In principle, practically any polymer can be converted into a foam product. Polymer foams may be classified as rigid or flexible depending on whether they are derived from polymers with glass transitions above or below ambient, respectively. The foams may be open or closed cell. They may be thermoplastic or thermoset; in the latter case, the polymer must be in a thermoplastic state while foaming is taking place. Foams made from hydrophilic polymers are generally classified as sponges — such as W. R. Grace's HY-POL ® which has fire retardant properties and is a particular embodiment of this invention. Polyurethane foams are widely used in medical and health care applications because fully cured polyurethane is chemically inert. Other specialty foams can be made from "functionalized" polymers — e.g., ionomers.

Some common examples of flexible foams include those made from neoprene, acrylonitrile-butadiene rubber, natural rubber, styrene butadiene rubber, polyetherurethane and silicone rubber. Common examples of rigid foams include polystyrene, polyurethane, epoxy, phenolic, polyethylene, polyetherurethane, PVC, silicone, cellulose acetate and urea-formaldehyde. Suppliers of these foam types are quite numerous as can be seen from a perusal of Thomas' Register of American Manufacturers.

Protective drapes comprised of a foam and a composite scrim may, thus, be stored dry and be "wet up" at a later time, preferably just prior to use. When fully "wet up," these drapes are quite effective in providing protection from exposure to high energy optical radiation, such as laser light, or other sources of harmful levels of heat. The "free" water of such embodiments functions as a heat sink, much like the "aquagels" described, further below in Section [4.4]. Moreover, after the initial absorption of thermal energy, the excess heat may be dissipated further by convection or evaporation of the water molecules. In the dry state, these protective drapes are much lighter in weight than the corresponding hydrogel drapes, simplifying and lowering the cost of packaging, handling, and transportation. These "dry" drapes are also expected to be considerably more stable than their water-saturated counterparts. Of course, fully "wet up" protective drapes may be stored, packaged, and shipped, if desired.

To prepare the protective drapes of the present invention, the porous polymer foam is integrated to a composite scrim by any number of methods, including but not limited to, bonding, spraying, coating, doctoring, layering, or extruding the integral elements. One may utilize a wide range of thicknesses for the foam component of the present protective drape. For instance, a layer of foam having a thickness in the range of about 10 to about 100 mil may be used in the present drapes. Preferably, the thickness lies in the range of about 15 to about 40 mil.

4.3. THE COMPOSITE SCRIM

An important aspect of the present invention concerns the modified scrim which is comprised of a sufficiently reflective, thermally conductive metallic component and a water-insoluble polymeric substrate. Most preferably, the water-insoluble polymeric substrate is hydrophobic. It has been discovered that the combination of a metal and any of a number of polymeric substances produces a scrim, which when incorporated into a hydrophilic gel, provides a protective drape superior in many ways with respect to laser stopping properties, stability and longer shelf-life, fire retarding characteristics, and processability, to name a few, in comparison with existing surgical drapes or laser shields.

The choice of the metallic component is of major importance in the present invention. Such a metallic component, or alloy thereof, must be able to withstand intense heat in a high humidity environment without destructive oxidation. Suitable metals, or alloys thereof, are preferably more reflective than absorptive or transmissive. However, if the metallic compound has absorptive characteristics, it should preferably have a high coefficient of thermal conductivity, k, such that any absorbed heat is quickly dissipated to the surrounding metallic area. Likewise, if the metallic component has a high degree of transmissive properties, the majority of such transmitted radiation should preferably scatter at an angle which allows the transmitted radiation to travel through the longest possible path in which hydrogel is present. Of course such metallic component must be processable with a polymeric substance to provide a composite material. In the present invention, a method which allows an investigator to determine the suitability of a particular metal or alloy is described in detail under Section 4.7. Examples of suitable metals or alloys include, but are not limited to, aluminum, copper, silver, gold, or brass, with copper being particularly preferred. Others which have been found to be unsuitable include titanium and stainless steel.

In selecting a suitable metallic component, it is important to keep in mind that it may be possible to balance the characteristics of reflectivity, thermal conductivity, and thickness of the metallic foil, sheet, or other suitable form of the metal. For instance, a material which is 100% reflective (i.e., all the energy of the incoming laser light is fully reflected) need only a very minimum amount of thermal conductivity, because there would not be a significant amount of heat absorbed which would need to be dissipated. On the other hand, if a metallic component has a relatively high degree of absorptivity (1-reflectivity), but has a high coefficient of thermal conductivity, one may be able to provide a foil or sheet which is sufficiently thick to exploit the highly conductive nature of the metal and thus dissipate the energy absorbed.

In general, materials which are suitable for $CO_2$ laser application will also work well with an Argon laser. However, copper metal does have a higher degree of absorptivity with respect to the wavelength of an Ar laser. Nevertheless, and as discussed supra, a sufficiently thick sheet or foil of copper will function effectively.

The polymeric substance is preferably selected from a water-insoluble hydrophobic synthetic polymer such as a polycarbonate, polyamide, polyester, polyolefin, poly(vinyl chloride), poly(4-methylpentene), polyacetylene, polyimide, fluoropolymer, polyvinylidene fluoride, polysulfone, polyether ether ketone, mixtures, blends, or copolymers thereof. Further, the composite scrim need not necessarily be a homogeneous material, but preferably may consist of layers of a polymer laminated metallic sheet or foil. It is important to note that the metallic component may be in any of a number of viable forms so long as the metallic parts are overlaid or are of sufficient concentration or density, such that no significant areas of the scrim are bare of the metallic component. Hence, besides a sheet (about 1 mil in thickness) or foil (about 0.3 mil in thickness) of metal, overlaid metallic plates, dense wire mesh, densely-packed finely-divided metallic particles, or the like may be equally useful. By the term "sheet" is meant that a certain material bears a sufficient amount of strength and thickness so as not to buckle under its own weight as it is cantilevered. However, the sheet should also have some degree of flexibility so that it will drape or conform to the surface (e.g., skin) on which it is laid. It should be noted that depending on the strength of the metal being used, a particular thickness may be sufficient to make a "sheet." In terms of convenience and availability, one can consider commercially available laminated metal foil or sheets, for example, aluminum mylar laminates.

Such composite polymer-foil laminates may comprise up to five or more layers. The central layer is composed of a metallic foil typically having a thickness ranging from about 0.2 mil to about 1 mil (1 mil=25.4 $\mu$m). It should be noted that thinner foils lack the physical integrity needed for processing, as well as the capability of dissipating heat away from the burn site. By contrast much thicker foils (or even some sheets) become too rigid to provide good draping or conformable characteristics. It should be noted, however, that the composite scrim can be manufactured with a plurality of metallic foils, each having at least the minimum prescribed effective thickness for that particular type of metal. Thus, if the effective thickness for a given metallic component ranges from, for example, 0.5 to 1.5 mil, a composite scrim having three layers of 0.5 mil thick foil is preferred over a single 1.5 mil thick layer. As mentioned previously, the metallic component preferably has a high coefficient of thermal conductivity which is best exploited by dissipating the absorbed heat, from an incident ray or flux of laser light, in a radial (r or in the plane of the metallic foil) direction away from the burn site. Utilizing the multilayered approach, the dissipation or conduction of heat in the direction of the incident beam (the z-direction) may be minimized by employing high-temperature, thermally nonconductive or poorly conducting adhesives to separate the individual metal foils. In such a manner, conduction in the r-direction is maximized while heat transfer in the z-direction is minimized. The thickness or amount of adhesive coating should be sufficient to promote adhesion but enough to separate the individual layers. Preferably, only the minimum amount is employed so that the least amount of degradable material is exposed to the high energy beam. Thus, the production of potentially corrosive or toxic by-products or gases, which may compromise the integrity of the composite scrim, is minimized. With the presence of a hydrogel or water-saturated foam, an even more effective dispersion or dissipation of heat away from the subject sought to be protected is obtained.

As noted earlier, the metallic component should ideally be more reflective than absorptive and have a high coefficient of thermal conductivity. The metal should preferably resist oxidation or degradation under high heat and high humidity environments and, also, possess a sufficiently high melting point. In particular, such a metallic component should be sufficiently stable to super heated steam and a focused laser. Preferably, especially with the multilayered composite scrims, the top layer of metallic foil (that one which is closest to the source of the laser light or the attending physician) has a matte finish. This dull finish can be imparted onto the metallic foil or sheet by a variety of ways including mechanical, chemical, or electrochemical means. More particularly, the matte finish may be obtained by texturizing, scratching, brushing, anodizing, etching (chemically or with a plasma), and like methods. Such treatment tends to lessen the amount of flashback associated with the impingement of laser light against a metallic surface.

The hydrophobic polymeric substrate undercoating of the composite scrims of the present invention may range in thickness from about 0.1 to about 3 mil. The undercoating of the laminate structure provides additional processing and/or handling strength to the scrim as well as other useful functions which are described further, below. Primarily, the polymeric substrate protects the metallic layer from long-term moisture (gel)-induced oxidation and/or corrosion. Preferably such a polymer has a high molecular weight, is capable of withstanding high heat and pressure, and has a certain amount of flexibility. A water-insoluble hydrophobic polymer topcoat may also be present. Such a topcoat may be about 0.05 to about 0.5 mil thick and should ablate freely under laser fire, leaving the exposed foil shiny and clean. Charring, or any decomposition process which leaves a residue, usually is undesirable due to the isolated absorption of laser energy by the residual organic matter. Also, such a topcoat should be substantially nonflammable under the conditions of the laser surgery.

In preferred embodiments of the present invention, the polymer substrate layers are bonded to the metallic component with high-temperature adhesive formulations, which may, themselves, be polymer-based. The process by which such adhesives are applied are well-known in the art and may include solution casting of the adhesive onto the polymeric substrate, compressing the metallic component to the treated polymeric substrate, followed by curing. A suitable adhesive should be applied to a thickness of about 0.1 mil, or less. Also, thin layers of additional coating (adcoat) of a polymer (e.g., PVC) may also be employed on one surface of the composite scrim, preferably on the side of the metallic component opposite the side in contact with the polymer undercoating. This additional polymeric coating prolongs the lifetime of the exposed portion of the metallic component. Several commercial metal laminates are listed in Table I.

TABLE I

COMMERCIAL METAL-POLYMER LAMINATES

| Entry[a] | Metal Component | Undercoat | Topcoat | Adhesive | Temp. Rating |
|---|---|---|---|---|---|
| 1. A15 | aluminum (0.35 mil) | P.E.T. (1 mil) | — | P.E.T.-based (0.1 mil) | 150° C. |
| 2. A10 | aluminum (0.35 mil) | P.E.T. (0.5 mil) | — | P.E.T.-based (0.1 mil) | 150° C. |
| 3. A35 | aluminum (0.35 mil) | P.E.T. (3 mils) | — | P.E.T.-based (0.1 mil) | 150° C. |
| 4. A17 | aluminum (0.7 mil) | P.E.T. (1 mil) | — | P.E.T.-based (0.1 mil) | 150° C. |
| 5. MFM555 | aluminum (0.35 mil) | P.E.T. (1 mil) | P.E.T. (0.5 mil) | P.E.T.-based (0.1 mil) | 150° C. |
| 6. KF150 | aluminum (0.35 mil) | Kapton ® (1 mil) | — | P.E.T.-based (1 mil) | >150° C. |
| 7. A15 adcoat | aluminum (0.35 mil) | P.E.T. (1 mil) | PVC (0.1 mil) | — | 150° C. |
| 8. PF57 | aluminum (0.7 mil) | Polypropylene (0.5 mil) | — | — | Ca. 150° C. |
| 9. C28 | copper (0.8 mil) | P.E.T. (2 mil) | — | P.E.T.-based | 150° C. |
| 10. 8910 | aluminum (0.35 mil) | P.E.T. (0.48 mil) | — | polyethylene-based (0.1 mil) | 66° C. |

[a]Entries 1-9 are available from Lamart Corp., Clifton, NJ and entry 10 is available from Lamotite, Inc., Cleveland, OH.

In one method to produce a specific embodiment of the present invention an aluminum mylar laminate (Lamart A-15) is coated on both sides with a viscous aqueous solution of poly(ethylene oxide), conveyed along a flat surface, and subjected to a dosage of high-energy electrons, produced by a Van de Graf generator, sufficient to crosslink the polymer chains of the poly(ethylene oxide). Viscoelastic hydrogels reinforced by a composite scrim result which may be used as a protective drape in a number of situations such as, for example, laser surgery, electrosurgery, or in any other circumstances in which an object or a person needs to be protected from extreme heat or a potential source of combustion such as an open flame. Additional layers of the composite scrim, variations in the configuration of the scrim, additional layers of hydrogel sheets, the incorporation of dense wire meshes, of various other additives, or the addition of backing materials are readily contemplated and are within the scope of the present invention. Wire meshes are particularly useful in minimizing injury due to "flashback" (more later).

Most typically, the protective drapes of the present invention provide ample protection in case of accident during laser surgery. Even if the incident laser beam, which has strayed accidentally, remains positioned at a particular spot for a moderate length of time, the subject's tissue will suffer little, if any, harm. The present drapes offer a two-staged layer of protection. First, the upper layer of hydrogel is burned off, releasing steam and non-toxic combustion gases. If the beam is sweeping at a moderate speed, most or all of the beam's energy is absorbed by the vaporizing upper layer of gel, and the foil is not exposed. If the beam is moving slowly, or is stationary, the upper layer of gel, and top coating over the foil are both burned off, exposing the foil. Much of the beam's energy is then reflected upwards and away from the patient. Energy absorbed by the foil is dispersed and attenuated by the thermal mass of the gel below the foil, protecting the patient from a local hot spot. The foil, in addition, radially dissipates the heat it absorbs.

The protective drapes of the present invention have a number of features which improve their performance over the known drapes utilizing only bare foil. Such features include, but are not limited to:

Drape

The added weight of a highly flexible gel improves substantially the adhesion to skin, conformability and "lay" of the drape. Bare foil and other thin, lightweight drapes can be easily disturbed by motion and air currents, and must be taped down at all edges.

Anti-flashback

Bare foil reflects almost all incident laser energy in a mirror-like fashion, placing all operating room personnel at risk directly, as well as indirectly through the ignition of nearby objects. Flashback from the herein described drape is reduced through several mechanisms. The laser beam must first erode a finite thickness of gel and top coat before the foil is exposed, delaying the onset of reflection. When the foil is uncovered, heat is transferred to the gel immediately surrounding the point of contact, causing the water to boil off. Vapor pressure below the foil causes its surface to distort upwards, creating a convex lens, scattering the incident beam, and decreasing the incidence of flashback. Since the foil is strengthened by its adhesively bound undercoat, distortion is allowable without bursting the foil.

Protection from Conductive Burns

At first contact with the top layer of gel, energy is absorbed and removed by a moving front of vaporizing gel. After ablation of the top gel layer, point contact heating is diffused and partially counteracted by intimate contact between the thermal mass of the gel and the foil-polymer laminate. Such thermal diffusion also occurs by radial heat transfer within the metallic component of the laminate itself.

Anti-glare

The addition of an opaque top liner, adcoat, and/or opaque additives to the gel eliminates reflected glare from the operating room lighting.

Processability/Stability

As described previously, bare metal drapes are extremely difficult to process resulting in the frequent tearing and wrinkling of the metal foil. The present drapes, are much easier to handle and, by contrast, suffer no detectable degradation or oxidation of the metallic component over extended periods of time (i.e., for at least 6 months).

The following discussions describe in further detail other possible configurations and embodiments of the present invention, the additional advantages of which will be readily apparent to one of ordinary skill.

In particular, a scrim configuration that has an intricate internal structure, such as a microporous membrane, has the added feature that an incoming beam of laser light can be deflected and defocused (i.e., effectively dispersed) within the internal structure of the scrim. For example, a slurry of finely divided metallic particles and a polymer (e.g., a polyester which is water-insoluble but soluble in an organic solvent such as N-methylpyrrolidone) dissolved in organic solvent along with a plasticizer, if necessary, is cast onto a flat surface to make a thin film. The entire flat surface can then be quenched in a water bath to produce a porous flexible flat structure due to the precipitation of the water-insoluble organic polymer. The metallic particles are entrapped in the polymer with a finite amount present on the surfaces (both internal and external) of the microporous structure. The resulting flexible porous sheet (the composite scrim) may then be immersed into a viscous solution of a hydrophilic crosslinkable water-soluble polymer (e.g., poly(ethylene oxide) and subjected to ionized radiation. The resulting protective drape would then have a hydrogel component in which is interspersed a microporous composite scrim.

Alternatively, a dense wire mesh sheet of sufficient thickness, which need not be of a composite nature, can be immersed, likewise, in a viscous solution of a crosslinkable water-soluble polymeric material. Hydrogel formation would give a protective drape having a metallic fibrous interior which is better able to internally dissipate an incoming beam of laser light compared with a flat sheet of, say, aluminum foil. As usual, the metallic component preferably has a higher coefficient of thermal conductivity in the radial direction, away from the burn site.

Suitable backing materials may comprise of thin sheets of low-density polyethylene, high-density polyethylene, polypropylene, poly(vinyl chloride), mixtures, blends, or copolymers thereof. In short, these materials may be derived from any poly(olefin). These polymers may also include appropriate antioxidants and/or plasticizing agents which are commonly used in the polymer art. Furthermore, these backing sheets may also be non-reflective and/or non-flammable. For example, blue-tinted, textured polyethylene sheets are particularly suitable for reducing the glare which may occasionally emanate from the metallic component of certain embodiments of the composite scrim. If desired, these backing materials may be permanently attached or bonded to the external surface of the hydrogel sheets. Conversely, they may be peeled from the protective drape, and the hydrophilic surface of the hydrogel may be applied directly to the surface of an object, the clothing of a person, or the skin of a patient.

4.4. NOVEL HYDROGELS WITH LIQUID AQUEOUS INTERIORS (AQUAGELS)

The effectiveness of the hydrogels in dissipating the heat generated by incident beams of laser light has to do, in a large part, with the high content of water present in these solid viscoelastic sheets. Because of the solid nature of the hydrogels, however, water molecules which evaporate in the vicinity of the path of the in-coming high energy optical beam are not replaced but continuously expand as a gas with eventual loss of the high heat capacity molecules. Such loss also results in a decrease in the ability of the hydrogel to dissipate heat by thermal conduction. Accordingly, in a particular embodiment of the present invention, a novel hydrogel material with a liquid center is disclosed, which novel hydrogel is able to constantly replace water molecules lost to evaporation in and around the path of the incident beam. Such a liquid-center hydrogel, referred to hereinafter as an "aquagel," is able to dissipate the heat generated by prolonged exposure of the hydrogel sheet to concentrated sources of laser light for much longer periods than conventional completely solid hydrogels and in combination with the composite scrim (vide infra) forms an effective protective drape.

The production of aquagels is accomplished by a procedure exemplified in Example 5.11 of the Example Section of this disclosure. This procedure is a modification of the general protocol of Example 5.1 and of the methods described, for example, in U.S. Pat. No. 4,684,558, and involves a controlled-depth irradiation step which is effective to crosslink the polymer chains at and near the surface of a liquid film formed from a viscous aqueous solution of a water-soluble crosslinkable polymer. The initially water-soluble polymer may be selected from any suitable polymer that is well-known in the art, including those recited previously, but is preferably a poly(ethylene oxide) polymer having an average molecular weight in the range of about $0.9 \times 10^6$. Further, the source of the flux of electrons may be operated at a voltage level in the range of about 0.15 to about 0.45 MeV, preferably about 0.18 to about 0.25 MeV. The overall dose of electron radiation to which the liquid film is exposed will vary somewhat depending upon the nature and amount of additives, if any, are present in the hydrogel formulation. Typically, however, the liquid film, in a poly(ethylene oxide) system, should be exposed to a minimum of about 0.5 Mrads to a maximum of about 5 Mrads.

4.5. ELECTROCONDUCTIVE PROTECTIVE DRAPES

A specific embodiment of the present invention incorporates within the hydrogel formulation an amount of a water-soluble electrolyte sufficient to reduce the electrical resistance of the overall protective drape and allow it to serve as an effective conducting medium. The resultant electroconductive protective drape may then be made into any shape or size, preferably large enough, say, to accommodate the conducting surface of a defibrillator paddle but not too large as to conduct the electrical charge over too large an area of the patient's chest. As most surgeons are aware patients undergoing surgery may suffer a cardiac arrhythmia or arrest without warning. One of the methods used by doctors in attempting to restore the sinus rhythm or to revive the heart of such a stricken patient is by electrical cardioversion in which a DC shock is applied to the patient through electrode paddles positioned on the chest and back (or side). Typically a conductive gel would normally be applied over the patient's skin before commencing the cardioversion procedure. Having a conductive hydrogel drape already positioned strategically during the surgical procedure would eliminate the need for these conductive gels and more importantly save precious seconds and minimize the onset of myocardial infarction. Although a simple electroconductive hydrogel would function well to transmit the electrical shock, in the context of the present invention, a protective drape comprised of an electroconductive hydrogel and a conductive composite scrim would serve both as a shield against direct, reflected, or stray laser light and as a localized pre-positioned conductive surface for electrical cardioversion. Preferably, the polymer laminate is comprised of a conducting polymer, such as iodide-doped polyacetylene or the like. Alternatively, the conductive hydrogel is part of a drape which utilizes a metallic sheet or mesh in place of a laminated metal foil. In yet another embodiment of the present invention, the conductive gel is slightly larger than the laminated portion of the drape thus providing an uninterrupted conductive path from the defibrillator pad to the patient's torso.

Preferably, the edges of the conductive protective drape are equipped with means for insulating the conductive drape from other materials positioned around the drape. The edges of the conductive drape could be lined, for example, by an insulating material such as siliconized rubber. The insulator would help in localizing the electrical charge to the area enclosed by the conductive drape and help prevent the "leakage" of the current to adjacent high-resistance protective drapes which because of their high water content and metallic component may nonetheless present a concern. Because the conductive protective drape is placed directly on the patient's skin, a conductive tacky and/or adhesive hydrogel formulation, such as that described in U.S. Pat. No. 4,706,680, is particularly advantageous. Other conductive hydrogel materials including those described in the Sieverding patents and the Anderson and Gunbusky patent, supra, may be used also.

4.6. METHOD FOR DETERMINING BURN-THROUGH TIMES

Purpose

To measure the relative resistance to burn-through of surgical drapes subjected to a $CO_2$ laser beam.

Scope

This method simulates use of a medical laser in the operating room, and can be used for any surgical drape intended for use as a laser shield.

Apparatus

1. $CO_2$ medical laser, capable of at least 40 watts power continuous (non-pulsed), using a focal length of 75-150 mm, and a spot size of less than 0.5 mm. Lasers satisfying these criteria include the Sharplan model 1040, and the Merrimack ML840.

2. A test stand designed to hold the laser stylus, test sample, and burn-through indicator in place without slip or vibration. The test stand may be vertical, such as a weighted lab clamp stand, or horizontal, such as an optical bench. The platform holding the sample under test must have a hole through its center, at least $\frac{3}{8}''$ in diameter. Distance between the laser stylus clamp and sample holding platform should be finely adjustable.

Figure 5A:
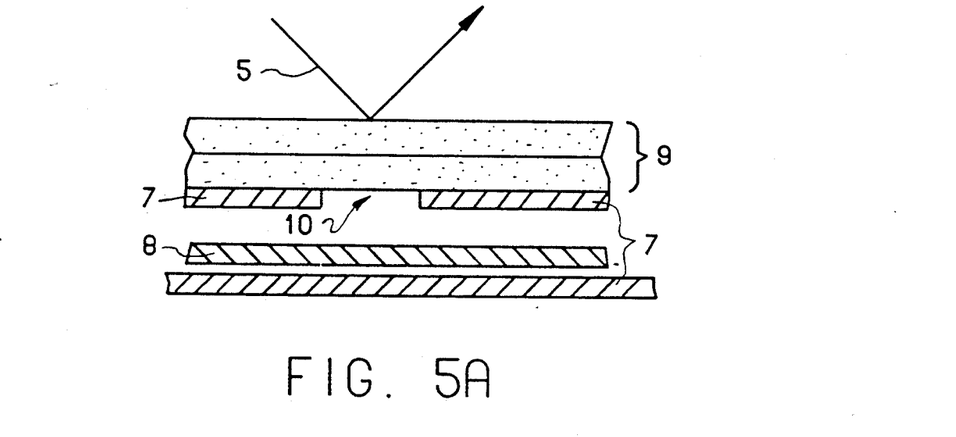
Figure 5B:
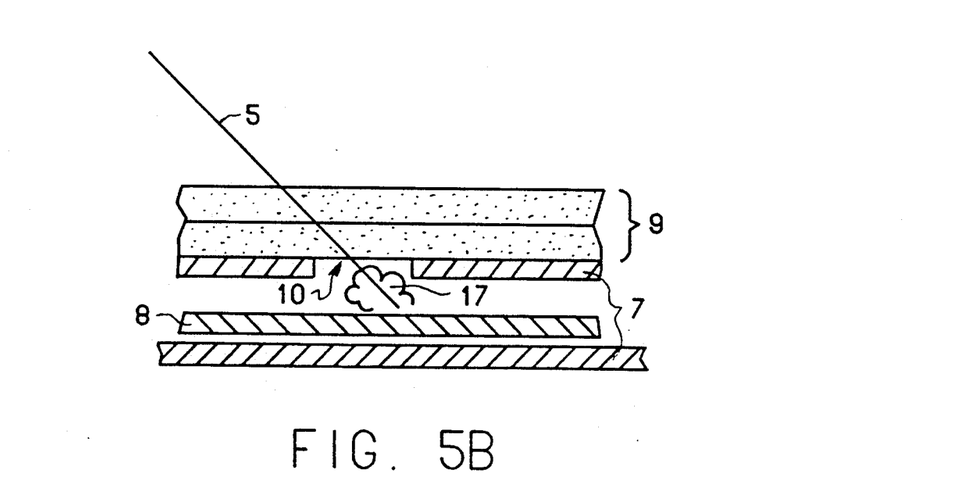

A second platform is placed behind the sample platform, such that a burn-through indicator may be placed in line with the laser and the hole through the sample platform, so that the laser beam will strike the indicator when no sample is present. The indicator should be placed 2 to 3 inches from the sample. (See, FIG. 5).

3. A burn-through indicator in the form of a thin strip of wood, such as a tongue depressor. Approximately one depressor is needed for each 5 trials.

Setup

Adjust the laser to provide 40 watts power, continuous beam. Clamp the laser stylus in place so that the beam axis is at a 45° angle to the sample platform, and so that the beam axis passes through the center of the hole in the platform. Adjust the distance between the sample platform and the laser stylus such that the laser beam focuses on the top surface of the test sample. The Sharplan 1040 has an indicator tip which extends past the end of the stylus, and terminates at the focal length. The distance between the sample and the indicator tip should be adjusted such that the indicator tip just touches the sample surface. If the laser stylus has no focus indicator tip, the focus point may be found by using the following procedure:

Place a tongue depressor on the sample platform, and adjust the distance from stylus to sample such that the tongue depressor is somewhat further away from the stylus than the focal point. Burn a series of holes in the tongue depressor, using a burn time of equal duration for each burn, and advancing the tongue depressor after each burn. Burn time should be short enough so that charring is minimized, and long enough so that the tongue depressor is completely punctured. Between burns, the sample platform should be moved by a small repeatable increment closer to the stylus. The burn hole size should diminish, then increase. The focus point is identified as that setting which produces the smallest diameter burn hole.

Test Cycle

Place a fresh tongue depressor on the burn indicator platform, positioned so that the locator beam of the laser hits it squarely, and is clearly visible. Trim the sample to a convenient size between $2'' \times 2''$ and $6'' \times 6''$ Place sample on the sample platform, reflective side up, positioned so as to completely cover the hole in the platform.

While observing the burn-through indicator, simultaneously fire the laser and start the stopwatch. At the first sign of light, smoke, or charring on the indicator, stop the stopwatch and extinguish the $CO_2$ laser beam. Record the burn-through time. Re-position both the sample and the burn-through indicator to allow the beam to hit an unused area.

Repeat Cycle

This test should be performed at least 3 times per sample. Additional repetitions may be advisable as necessary.

4.7. METHOD FOR DETERMINING SUITABILITY OF A PARTICULAR METALLIC COMPONENT

Figure 6A:
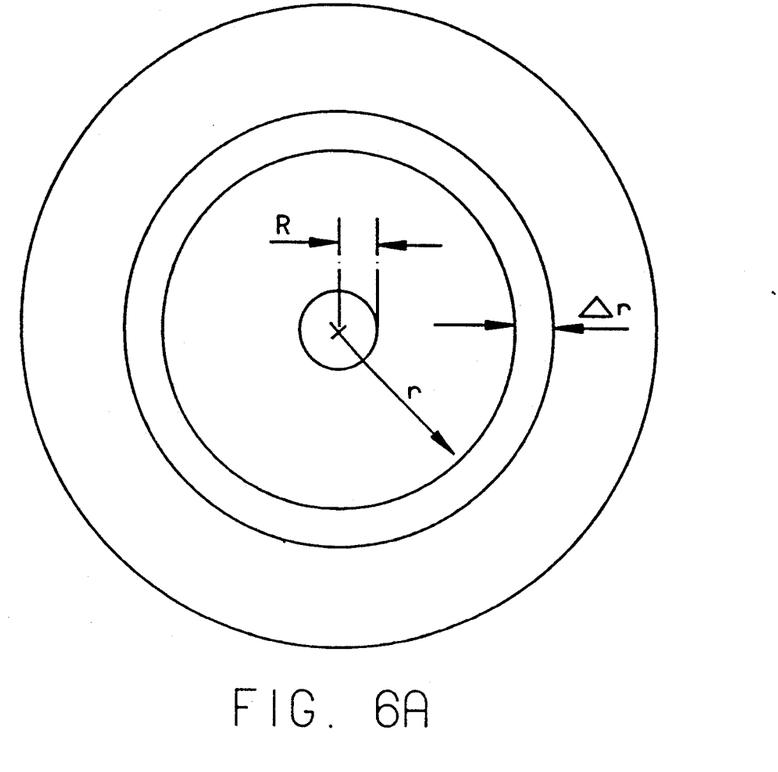
Figure 6B:
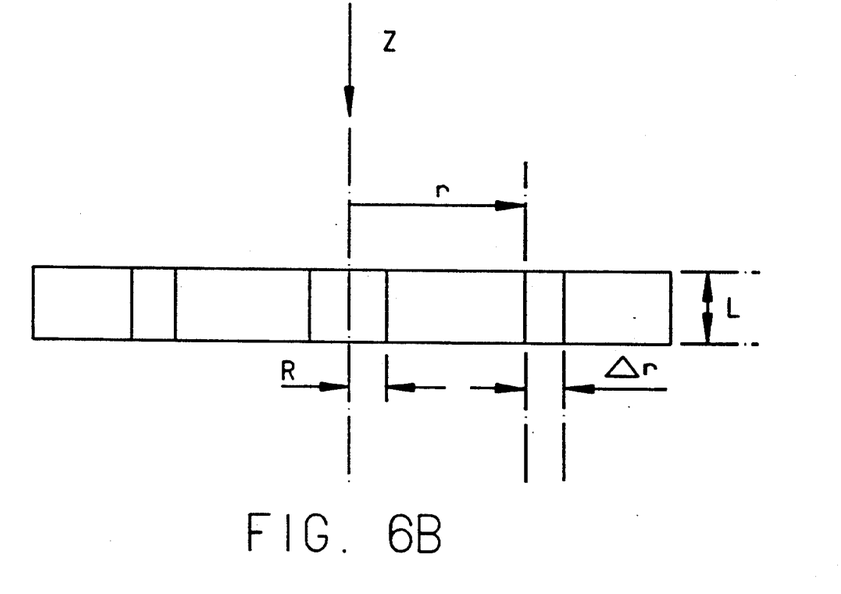
FIG. 6B shows a side view of which r is the radius of incremental element $\Delta r$.
Figure 7:
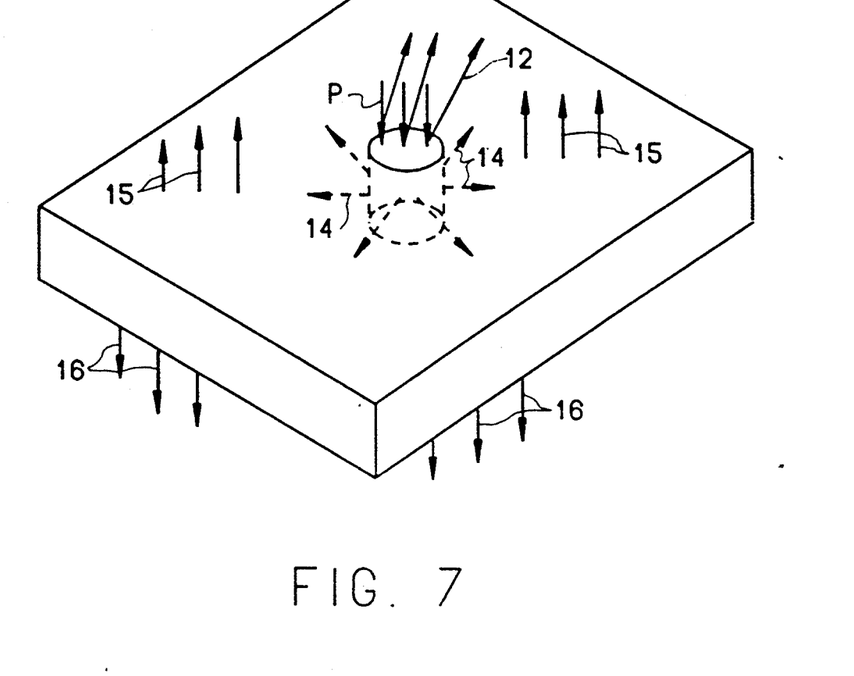
FIG. 7 illustrates the area of the incidence of the laser beam striking the metallic component and the resulting dissipation of energy as described in Section 4.7. In this illustration, P is the impinging laser column, 12 is the reflected beam, 14 is the radial heat flux, 15 is the heat flux to the top of the hydrogel and 16 is the heat flux to the bottom of the hydrogel.
Figure 8:
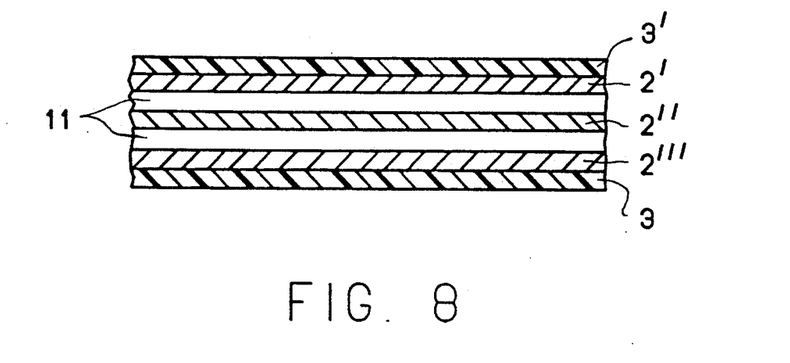
FIG. 8 illustrates one embodiment of a multilayered composite scrim in which three metallic foils, 2′ (having a matter finish), 2″ (having a neutral finish), and 2‴ (having a mirror finish) each separated by a high-temperature adhesive, 11, are interposed between a first hydrophobic polymeric substrate, 3 (e.g., mylar), and a second hydrophobic polymeric substrate, 3′ (e.g., PVC).

A method of analysis to determine the suitability of a candidate metal sheet or foil uses a laser ray of a given diameter (2R) operating at a power (P'). This uniform flux $P'/\pi R^2$ drives heat into the metal sheet at a flux of $P/\pi R^2$ where P is the absorbed fraction of power$=(1-\rho)P'$ and $\rho$ is the reflectance of the metal to the particular laser light. At steady state conditions, which would constitute the maximum temperature achieved in the vicinity of the laser flux, heat is dissipated from the impinged cylinder by reflection in the transverse direction and by conductive heat transfer in the radial direction away from the cylinder. This radial heat transfer specifically depends upon the thermal conductivity k of the metal and upon its thickness L. The conducting metal itself is further cooled by losing heat to the hydrogel that is in intimate contact with it by conductive heat transfer in the transverse direction into each surrounding hydrogel. This heat flux is proportional to the heat transfer coefficient, h, and the local temperature difference between the metal and the exterior of the gel and the area of contact of the element considered.

If it is proposed that all of the heat entering the laser shield radially transfers away from the source, a heat balance on an annular ring radius r and thickness $\Delta r$ gives the following expression $$\Delta(qr)L + 2hr\Delta r(T-T_o) = 0$$

where q is the heat flux in the radial direction at radius r in the first term and the second term is an expression for the heat dissipated in the traverse direction into the surrounding gel. This difference equation can be converted into a differential equation by allowing $\Delta r$ to approach zero. The resulting differential equation, utilizing appropriate boundary conditions, can be solved by well known techniques as enumerated in major texts on heat transfer for example "Conduction Heat Transfer" by V. Arpaci, Addison-Wellsley, Reading, Mass., (1966) or "Conduction of Heat in Solids" by Carslaw and Jeager, Oxford University Press (1959). The solution to the differential equation is of the form $$T - T_o = c_1 I_o\left[\left(\frac{2h}{KL}\right)^{\frac{1}{2}} r\right] + c_2 K_o\left[\left(\frac{2h}{KL}\right)^{\frac{1}{2}} r\right]$$

where
$T_o =$ ambient temperature
$I_o$ and $K_o$ are modified Bessel functions of the first and second kind respectively each of order zero.
$c_1$ and $c_2$ are constants The constants can be readily determined from the two boundary conditions (1) the heat flux leaving the cylindrical element impinged by the laser is equal to the total heat flux absorbed $$2\pi RLk \frac{dT}{dr} = -P \text{ at } r = R$$

and (2) at very large distances from the center point of the laser impingement the temperature is finite. Using these conditions we find that $c_1 = 0$ and $$c_2 = \frac{P}{2\pi RLk\left(\frac{2h}{KL}\right)^{\frac{1}{2}}} / K_1\left[\left(\frac{2h}{KL}\right)^{\frac{1}{2}} R\right]$$

This results in a temperature profile expressed as follows $$T - T_0 = \frac{P}{2\pi RLk\left(\frac{2h}{KL}\right)^{\frac{1}{2}}} \frac{K_0\left[\left(\frac{2h}{KL}\right)^{\frac{1}{2}} r\right]}{K_1\left[\left(\frac{2h}{KL}\right)^{\frac{1}{2}} R\right]},$$

at $R < r < \infty$

For a given laser operating at a specific power P' and operating at a specific flux determined by R, the choice of a particular metal, including its thickness can be made by evaluating the temperature profile above and observing the temperature at r=R. Then for a given metal i $$\max(T - T_0) = \frac{(1 - \rho_i) P'}{\left(\frac{2h}{K_i L_i}\right)^{\frac{1}{2}} (k_i L_i) 2\pi R} \frac{K_0\left[\left(\frac{2h}{K_i L_i}\right)^{\frac{1}{2}} R\right]}{K_1\left[\left(\frac{2h}{K_i L_i}\right)^{\frac{1}{2}} R\right]}$$

described a system at least as good as the systems described in the Example Section (e.g., Examples 5.2 and 5.3). Another restraint must be that the melting point of the instant metal must be greater than T. Also for proper drapability $E_i L_i^3 \leq E_{Al} l_{Al}^3$ where $E_i$ is the modulus of elasticity of the considered metal and $E_{Al}$ is the modulus of elasticity of aluminum.

As before, a term $I_n(mx)$ is used to described a modified Bessel function of the first kind of order n, and $K_n(mx)$ signifies a modified Bessel function of the second kind of order n.

The results of such calculations using some representative metals are given in Table II. As is evident from Table II, titanium is a poor choice for the metallic component as a prohibitively thick sheet is needed to provide adequate protection from the heat associated with an incident beam of laser light.

TABLE II

PARAMETERS CONTROLLING LASER
BLOCKING PERFORMANCE OF VARIOUS
METALLIC FOILS USED AS COMPONENTS
IN A COMPOSITE SCRIM

| Metal | k | r | $T_m$ | $L_{min}$ |
|---|---|---|---|---|
| Aluminum | 2.37 | 98.0% | 660 | 0.35 |
| Copper | 3.98 | 98.8% | 1083 | 0.10 |
| Silver | 4.27 | 99.1% | 962 | 0.06 |
| Gold | 3.15 | 97.4% | 1064 | 0.40 |
| Titanium | 0.2 | 90.6% | 1660 | 50.00 |

Definition of terms:
k = Thermal conductivity in watts/(cm degree c)
r = Reflectivity at 10.6 microns (Carbon dioxide laser wavelength)
$T_m$ = Melt temperature in degrees C.
$L_{min}$ = Minimum thickness in mils required to give adequate laser blocking.

5. EXAMPLES

Specific embodiments of the present invention are described in detail in the Example Section below. These examples are to be considered for illustrative purposes only and are not to be construed as limiting the scope and spirit of the invention.

5.1. PROTECTIVE DRAPE HAVING A HYDROGEL WITH TACKY AND ADHESIVE PROPERTIES

A first liquid film approximately 28 mils thick comprised of a 10.5 weight percent aqueous solution of poly(ethylene oxide) (PEO) and having an average molecular weight of about $0.9 \times 10^6$ Daltons is cast onto a thin sheet (ca. 1.0 to 1.5 mil) of low density polyethylene backing material. A scrim of aluminum/mylar laminate, comprising a poly(ethylene terpthalate) (P.E.T.) film (1.0 mil in thickness), aluminum foil (0.35 mil), and an adhesive (0.1 mil), usually derived from a heat curable thermosetting polyester, and which aluminum/mylar laminate has planar dimensions comparable to the backing material and first aqueous PEO liquid film, is laid over the viscous PEO solution. A second aqueous PEO film, approximately 28 mils thick, is cast over the aluminum/mylar laminate scrim and is, in turn, covered by a blue-tinted sheet of low-density polyethylene having a textured surface. The resultant layered structure is next passed under the beam of a Van De Graf Generator operated at a voltage of 1.5 MeV. The layered structure receives a total dose of about 0.4 Mrad, sufficient to crosslink both layers of PEO.

Alternatively, the aluminum/mylar laminate sheet is immersed into an aqueous solution of the poly(ethylene oxide), and the coated scrim is then covered on both sides by polyethylene backing materials. The layered structure is then exposed to the ionizing radiation as described above.

The protective drape, thus produced, has the adhesive, tacky, and cohesive characteristics of the hydrogel layers. More importantly, such a protective drape is able to serve as a barrier against extreme heat or the destructive effects of a laser for a finite period of time, typically greater than 30 seconds in the case of a $CO_2$ laser.

5.2. PROTECTIVE DRAPE HAVING A HYDROGEL WITH TACKY ADHESIVE PROPERTIES, ENHANCED LASER SCATTERING, AND EXTENDED SHELF LIFE

A hydrogel drape is produced in a similar fashion to that described in Example 5.1, except the aqueous solution of PEO contains suspended in it 0.05 wt % titanium dioxide powder, with a particle size spectrum peaking near the wavelength of the laser to be used. In addition, the scrim used is a tri-laminate composed of 0.35 mil Aluminum foil, 1.0 mil poly(ethylene terepthalate) (P.E.T.) undercoating, bonded to the dull side of the aluminum by a P.E.T.-based adhesive, and a top-coating of 0.1 mil poly(vinyl chloride) (PVC). The drape, thus produced, exhibits all the properties of Example 5.1, with the following enhancements: a longer shelf life, caused by the isolation of the foil from the gel by the addition of the PVC top-coat. Improved scattering of incident laser light, due to the addition of titanium dioxide. A burn-through time greater than 30 seconds is observed.

5.3. STERILE PROTECTIVE DRAPE HAVING A HYDROGEL WITH NON-STRINGY PROPERTIES, ENHANCED LASER SCATTERING, AND EXTENDED SHELF LIFE

A drape is prepared as in Example 5.2 and packaged in an airtight, moisture-proof, heat-sealable pouch. The packaged drape is then irradiated by an electron beam of voltage 4.5 MeV, at a dose of 2.5 Mrads. The extended dosage, combined with the nature of the hydrogel polymer, provides a non-stringy gel surface whose use is not associated with any objectionable sensation. A burn-through time of $>30$ seconds is observed with this drape.

5.4. PROTECTIVE DRAPE HAVING A HYDROGEL WITH INCREASED WATER CONTENT

A drape is prepared as in Example 5.1 or 5.2, except using a 4 wt % aqueous solution of PEO having an average molecular weight of about 4 million Daltons. This formulation decreases adhesion, but improves the ability of the drape to withstand protracted laser fire. Burn-through time: $>30$ seconds.

5.5 PROTECTIVE DRAPE HAVING A HYDROGEL WITH THICK ALUMINUM TRI-LAMINATE SCRIM

A drape is prepared as in Example 5.1, 5.2, or 5.3, except that a composite scrim comprising 1.0 mil aluminum sheet, laminated to 0.1 ml of PVC on both sides is employed. Local heating is reduced further, as the improved conduction of a thicker foil rapidly disperses hot spots.

5.6. PROTECTIVE DRAPE EMPLOYING A THICK COPPER TRI-LAMINATE SCRIM

A drape is prepared as in Example 5.5, except that the metallic component used comprises a 1.0 mil copper sheet. This drape has excellent resistance to burn-through for infared lasers, due to the high reflective coefficient of copper in the far infared. Local heating is reduced, as the high thermal conductivity of copper rapidly disperses hot spots. Burn-through time is at least about 30 seconds.

5.7. PROTECTIVE DRAPE EMPLOYING A POLYPROPYLENE SCRIM

The drapes of the preceding examples are also prepared using polypropylene laminated metallic sheets. A copper sheet, 1.0 mil in thickness, is undercoated with a 0.7 mil thick film of polymer using a high-temperature adhesive. A topcoat of 0.1 mil thick polymer is then applied over the metal sheet. The topcoat may be polypropylene, poly(vinyl chloride), or any other type of high molecular weight water-insoluble polymer. Burn-through time: about 30 seconds.

In general, it should be kept in mind that the principal purpose of the topcoat is to protect the metallic component from corrosion due to intimate contact with the aqueous gel. This purpose should be achieved with as thin a topcoat as possible so as not to provide a source of potentially combustible material. Ideally, the topcoat should just "ablate" away upon exposure to the laser light and not char or ignite. On the other hand, the undercoat's principal purpose is to protect the metallic component against the undesirable consequences of long-term contact with the gel, wrinkling or tearing during processing and/or handling, and bursting (in the direction towards the laser source) upon exposure to laser energy. Thus, depending upon the type of polymeric substrate employed, the bottom or undercoat is usually as thick or thicker than the topcoat.

5.8 STERILE ADHESIVE PROTECTIVE DRAPE EMPLOYING AN AQUEOUS SOLUTION OF POLY(VINYL PYRROLIDONE) (PVP)

The previous drapes of various configurations are also prepared using a 20 wt % PVP (grade K-90, $M_w \sim 1 \times 10^6$ Daltons) hydrogel. The initial aqueous solution of PVP contained biocides in the following concentrations, by weight: Methyl paraben, 0.18%; Propyl paraben, 0.05%; Ethyl paraben, 0.03% Butyl paraben, 0.01%; Dowicil 200(R), 0.1%. The drape is then irradiated until it receives a primary dose of approximately 1.0 Mrad (1.5 MeV source). The drape is then packaged in an airtight, moisture-proof, heat-sealable pouch. Subsequently, the packaged drape is irradiated with an electron beam of voltage 4.5 MeV, at a dose of 2.5 Mrads. The resultant sterile drape is adhesive with moderate tack (See, Section 5.3).

5.9. PROTECTIVE DRAPE EMPLOYING AN AQUEOUS SOLUTION CONTAINING A BLEND OF POLY(VINYL PYRROLIDONE) (PVP) AND POLY(ETHYLENE OXIDE) (PEO)

The drape of any of the previous examples may also be prepared with a polymer blend comprising PVP, grade K-90 ($M_w \sim 1 \times 10^6$ Daltons) at a 20% concentration by weight, and PEO at a 1% concentration by weight and having an average molecular weight of $0.9 \times 10^6$ Daltons. The aqueous solution may also contain biocides in the following concentrations by weight: Methyl paraben, 0.15%; Propyl paraben, 0.02%; Butyl paraben 0.007%; Ethyl paraben 0.02%; Dowicil 200 ®, 0.1%. The primary dose for preparing the hydrogel drape is approximately 1.4 Mrads, as applied by the electron beam of a Van de Graf generator operating at a potential of 1.5 MeV.

5.10. CONDUCTIVE PROTECTIVE DRAPE HAVING A HYDROGEL WITH TACKY AND ADHESIVE PROPERTIES, AND EXTENDED SHELF LIFE

Hydrogel drape is produced in a similar fashion to Example 5.2, except the aqueous solution of PEO used in the hydrogel formulation also contains as an electrolyte, 5% potassium chloride by weight. In addition, the foil scrim employed is slightly undersized with respect to the dimensions of the gel and liners. This product exhibits all the advantages of Example 5.2 and, in addition, provides a conductive path for a cardioversion procedure when both liners are removed. Note that with the top liner removed, the pigmented gel substantially reduces glare as compared to clear gel. Also, a conductive laminated scrim is produced using a conductive polymer such as doped poly(acetylene). Burn-through time: >30 seconds.

5.11. PROTECTIVE DRAPE HAVING A LIQUID CENTER

A protective drape with a liquid center is prepared by the following procedure. The initial assembly of the uncrosslinked drape sheet is identical to Example 5.1. Primary irradiation is provided by an electron beam with energy of 1.5 MeV. A water-cooled metallic mask of sufficient thickness to completely absorb incident electron radiation (approximately 8 Kg/square meter) is placed between the beam and the uncrosslinked wet sheet, such that only the outer edges of the sheet receive a crosslinking dose. At this point the aqueous liquid center is bounded by liners above and below the crosslinked outer gel region with the foil-polymer scrim in the very center. The sheet is then optionally subjected to a controlled-depth irradiation on both sides, using a low-energy electron beam of approximately 250 KeV, at a surface dose sufficient to crosslink the solution to a depth about 10 mil from each liner. Since the dose-depth gradient of the electron beam at these energies falls off sharply, the outer skin will be highly crosslinked, whereas the center will be completely uncrosslinked, having received no dose. The resultant sheet may be cut across the web where it is crosslinked through its full depth and sealed mechanically, with tape or other means. The resultant drape has extended durability under fire, because the aqueous solution, unlike the solid gel, is replaced upon vaporization, allowing additional heat to be removed harmlessly from the point of contact with the laser beam. Burn-through time is about 30 seconds.

5.12. DECREASED FLASHBACK WITH METALLIC MESHES ON TOP OF COPPER SCRIM

A drape is prepared as in example 5.7, except for the addition of a fine metallic mesh scrim placed above the foil-polymer laminate. The mesh may be applied as a top liner in place of the polymeric film, or placed between the foil laminate and the upper layer of gel. In the second configuration, an adhesive, preferably a thin film of gel, is first coated onto the foil laminate. The mesh should have a dense multi-layer weave such that a direct line of sight through the mesh is minimized, or non-existent.

This particular drape substantially diminishes flashback, in the following manner: the metallic mesh is punctured by the downward passage of the laser beam. The reflected beam is not powerful enough to pierce the mesh upon exit, and is scattered and attenuated, thus reducing flashback. Burn-through time is about 30 seconds or less.

5.13. DOUBLE FOIL TO GIVE ADDED PROTECTION AFTER INITIAL BURN-THROUGH

Figure 1:
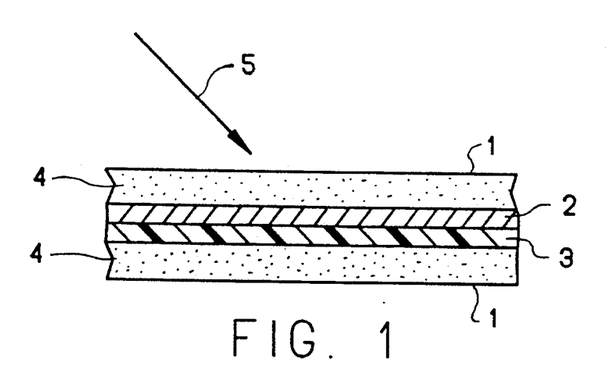
FIG. 1 illustrates one embodiment of the present invention, hydrogel sheet with laminated foil/sheet, having a composite scrim which comprises a reflective metallic foil or sheet (2) and a polymeric laminate (3). Selected backing materials (1) enclose the crosslinked hydrogel (4). Incident laser light (5) strikes the top surface of the protective drape.
Figure 2:
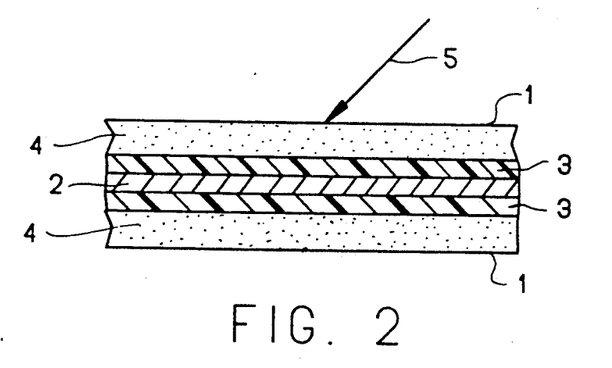
FIG. 2 illustrates one configuration of a hydrogel sheet that utilizes a trilaminate scrim having two polymeric coatings, one on each face of the metallic component.
Figure 3:
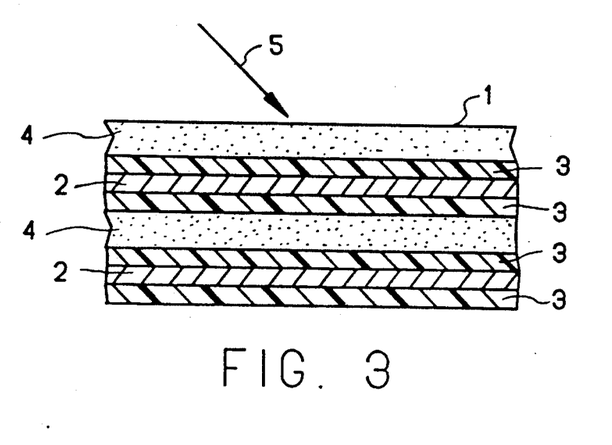
FIG. 3 illustrates another embodiment, a double trilaminate hydrogel, which employs a trilaminate as internal scrim as well as bottom backing material.
Figure 4:
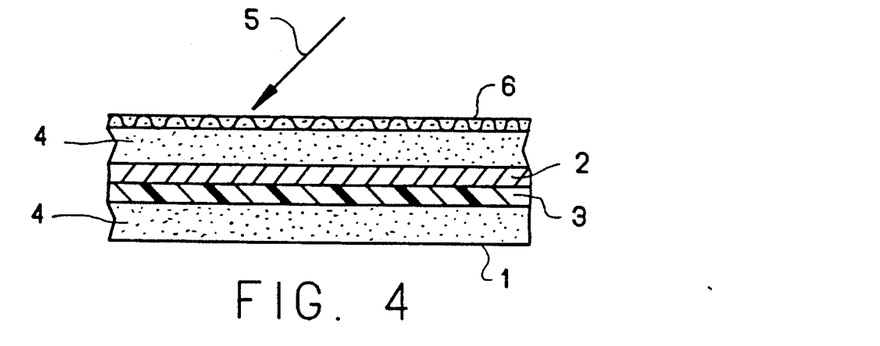
FIG. 4 illustrates a protective drape with a top backing comprising a wire mesh (6) for greater deflective power and anti-flashback characteristics.

The drapes of any of the previous examples may also be constructed with a foil-polymer laminate substituting for the bottom liner (See, for example, FIG. 3). This laminate may be top-coated for protection against corrosion, as in Example 5.7. This configuration gives added protection against burn-through, as follows: if the laser beam succeeds in penetrating through the top layer of foil, it will then ablate through the second layer of gel, and then reflects from the bottom foil layer. Although the second layer of foil will create a "hot spot" in this instance, the patient is shielded from direct laser fire for a protracted period of time. Burn-through time: greater than 1 minute.

5.14. NONFLAMMABILITY OF PROTECTIVE DRAPES

The protective drapes of the present invention are subjected to two sets of experimental conditions. First, the present drapes are exposed to stationary beams of laser light as described previously under Section 4.5, as well as swept beams of such light. None of the particular embodiments of the present drapes ignited during the laser experiments. Indeed, a flexible solid sheet of a viscoelastic hydrophilic gel comprising a homogeneous mixture of at least about 90% by weight of water in a substantially water-insoluble, water-swellable hydrophilic polymer failed to ignite under these same test conditions.

Second, the present drapes and a simple flexible solid sheet of a viscoelastic hydrophilic gel comprising a homogeneous mixture of at least about 90% by weight of water in a substantially water-insoluble, water-swellable hydrophilic polymer are subjected to the small flame test which is described in UL test method 214, Underwriters Laboratories, Northbrook, Ill. None of the materials tested ignited. Furthermore, combustible materials, such as cellulosics, which are covered intimately with the present drapes or a simple hydrogel, as described herein, and which are then subjected to the same experimental conditions as those described above, show a marked decrease in their tendency to ignite relative to the unprotected combustible materials.

What is claimed is:

1. A protective drape comprising:
   (a) at least one flexible solid sheet of a viscoelastic hydrophilic gel comprising a homogeneous mixture of at least about 80% by weight water and a substantially water-insoluble, water-swellable, hydrophilic polymer; and
   (b) at least one flexible composite scrim comprising a laminate of at least one foil or sheet of a metallic component and at least one film of a hydrophobic polymeric substrate, said scrim being in intimate contact with said flexible solid sheet and which metallic component has a sufficient degree of reflectivity, thermal conductivity, and thickness, to provide a protective drape having top and bottom external surfaces, which drape is capable of effectively dissipating thermal energy associated with an accidentally directed beam of laser light.

2. A protective drape comprising:
   (a) at least one flexible solid sheet comprising a porous polymer foam; and
   (b) at least one flexible composite scrim comprising a laminate of at least one foil or sheet of a metallic component and at least one film of a hydrophobic polymeric substrate, said scrim being in intimate contact with said foam and which metallic component has a sufficient degree of reflectivity, thermal conductivity, and thickness, to provide a protective drape having top and bottom external surfaces, which drape upon wet up by swelling the foam is capable of effectively dissipating thermal energy associated with an accidentally directed beam of laser light.

3. The protective drape of claim 1 or 2 in which said foil or sheet of said metallic component of said laminate is oriented toward said top external surface of said drape and said solid sheet is oriented toward said bottom external surface of said drape.

4. The protective drape of claim 1 or 2 in which said composite scrim is substantially enclosed by said solid sheet.

5. The protective drape of claim 1 or 2 in which said composite scrim is interposed between a pair of said solid sheets.

6. The protective drape of claim 5 in which the first of said pair of solid sheets is oriented toward the top external surface of said drape and the second of said pair of solid sheets is oriented toward the bottom external surface of said drape, said second solid sheet being thicker than said first solid sheet.

7. The protective drape of claim 1 or 2 in which said composite scrim comprises a trilaminate in which at least one foil or sheet of said metallic component is interposed between a pair of said films of said hydrophobic polymeric substrate.

8. The protective drape of claim 7 in which said trilaminate is oriented toward said top external surface of said drape and said solid sheet is oriented toward said bottom external surface of said drape.

9. The protective drape of claim 7 in which said trilaminate is substantially enclosed by said solid sheet.

10. The protective drape of claim 7 in which said trilaminate is interposed between a pair of said solid sheets.

11. The protective drape of claim 10 in which the first of said pair of solid sheets is oriented toward the top external surface of said drape and the second of said pair of solid sheets is oriented toward the bottom external surface of said drape, said second solid sheet being thicker than said first solid sheet.

12. The protective drape of claim 1 or 2 in which a pair of said composite scrims and a pair of said solid sheets form alternating overlapping layers.

13. The protective drape of claim 12 in which one of said pair of composite scrims is oriented toward said bottom external surface of said drape and one of said pair of solid sheets is oriented toward said top external surface of said drape.

14. The protective drape of claim 12 in which at least one of said pair of composite scrims comprises a trilaminate.

15. The protective drape of claim 13 in which at least one of said pair of composite scrims comprises a trilaminate.

16. The protective drape of claim 7 in which said trilaminate is asymmetric such that the first of said pair of said hydrophobic polymeric substrate films is oriented toward the top external surface of said drape and the second of said pair of said hydrophobic polymeric substrate films is oriented toward the bottom external surface of said drape, said second film being thicker than said first film.

17. The protective drape of claim 11 which further comprises a second trilaminate composite scrim in intimate contact with said second solid sheet, at least one of said trilaminates being asymmetric.

18. The protective drape of claim 1 or 2 in which said composite scrim comprises a laminate of two or more foils or sheets of said metallic component, a high-temperature adhesive which is substantially thermally non-conductive and which is interposed between each of said foils or sheets, and at least one film of a first hydrophobic polymeric substrate.

19. The protective drape of claim 18 in which said composite scrim further comprises at least one additional film of a second hydrophobic polymeric substrate.

20. The protective drape of claim 1 or 2 which further comprises at least one backing material in intimate contact with at least one of said external surfaces of said drape.

21. The protective drape of claim 1 or 2 which further comprises a first backing material and a second backing material, the first in intimate contact with said top external surface of said drape and the second in intimate contact with said bottom external surface of said drape.

22. The protective drape of claim 21 in which said first backing material is nonreflective.

23. The protective drape of claim 21 in which said first backing material is nonflammable.

24. The protective drape of claim 20 in which said backing material is derived from a poly(olefin).

25. The protective drape of claim 1 or 2 which further comprises a dense wire mesh in intimate contact with said metallic component of said laminate.

26. The protective drape of claim 1 or 2 which further comprises a dense wire mesh in intimate contact with said top external surface of said drape.

27. The protective drape of claim 7 which further comprises a dense wire mesh in intimate contact with said trilaminate, in which said mesh is oriented toward the top external surface of said drape.

28. The protective drape of claim 1 in which said flexible solid sheet is an aquagel comprising a viscoelastic hydrophilic gel having a liquid center.

29. The protective drape of claim 1 in which said composite scrim is interposed between a pair of said flexible solid sheets, at least one of said solid sheets, preferably that one which is oriented toward the top external surface of said drape, is an aquagel.

30. The protective drape of claim 1 in which said hydrophilic polymer has an initial average molecular weight of at least about $0.1 \times 10^6$ Daltons.

31. The protective drape of claim 1 in which said hydrophilic polymer is a mixture of polymers having an initial average molecular weight in the range of about $0.1 \times 10^6$ to about $10 \times 10^6$ Daltons.

32. The protective drape of claim 1 in which said hydrophilic polymer is an initially water-soluble polymer crosslinked by a process selected from the group consisting of chemical and irradiation crosslinking.

33. The protective drape of claim 1 in which said hydrophilic polymer is an initially water-soluble polymer made water-insoluble by crosslinking, which initially water-soluble polymer is selected from the group consisting of poly(ethylene oxide), hydrolyzed or partially hydrolyzed acrylonirite, hydroxy-modified celluloses, polyacrylamide, poly(vinyl pyrrolidone), poly(vinyl alcohol), mixtures, blends, and copolymers thereof.

34. The protective drape of claim 1 in which said hydrophilic polymer is an irradiation crosslinked poly(ethylene oxide).

35. The protective drape of claim 1 in which said viscoelastic hydrophilic gel is comprised of a homogeneous mixture of water and about 2 to about 20 weight percent of the total mixture of poly(ethylene oxide) having an average molecular weight of about $0.1 \times 10^6$ to about $10 \times 10^6$ Daltons, said mixture having been exposed to a dosage of high energy radiation of about 0.2 to about 4 Mrads, sufficient to crosslink said poly(ethylene oxide).

36. The protective drape of claim 1 in which said viscoelastic hydrophilic gel further comprises an additive selected from the group consisting of pigments, refractive particles, fire retardants, stabilizers, electrolytes, preservatives, biocides, dyes, and mixtures thereof.

37. The protective drape of claim 1 in which said viscoelastic hydrophilic gel further comprises finely-divided particles of a metal oxide selected from the group consisting of titanium dioxide, zirconium dioxide, silicon dioxide, aluminum oxide, molybdenum oxide, zinc oxide, and mixtures thereof.

38. The protective drape of claim 2 in which said porous polymer foam is derived from a hydrophilic polymer.

39. The protective drape of claim 2 in which said porous polymer foam is derived from a hydrophobic polymer.

40. The protective drape of claim 39 in which said porous polymer foam has been modified to provide water-wettable surfaces.

41. The protective drape of claim 2 in which said porous polymer foam is derived from a hydrophilic polymer selected from the group consisting of foamable hydrophilic polyurethanes, polyurethanes, cellulose acetate, and cellulosic sponges.

42. The protective drape of claim 1 or 2 in which said metallic component may, alternatively, be in a form selected from the group consisting of a dense wire mesh, interconnected plates, densely packed finely-divided particles, and combinations thereof.

43. The protective drape of claim 1 or 2 in which said metallic component is selected from the group consisting of aluminum, copper, gold, silver, and brass.

44. The protective drape of claim 1 or 2 in which said metallic component is derived from aluminum.

45. The protective drape of claim 1 or 2 in which said metallic component is derived from copper.

46. The protective drape of claim 1 or 2 in which said hydrophobic polymeric substrate is a polymer selected from the group consisting of polycarbonate, polyamide, polyester, polyolefin, poly(vinyl chloride), poly(4-methylpentene), polyacetylene, polyimide, fluoropolymer, polyvinylidene fluoride, polysulfone, polyether ether ketone, mixtures, blends, and copolymers thereof.

47. The protective drape of claim 1 or 2 in which said composite scrim is a laminate comprising at least one foil or a sheet of aluminum and at least one film of poly(ethylene terpthalate).

48. A protective drape of claim 18 in which said high-temperature adhesive is selected from the group consisting of acrylics and poly(ethyleneterpthalate) adhesives.

49. A protective drape comprising:
(a) at least one flexible solid sheet of a viscoelastic hydrophilic gel comprising a homogeneous mixture of at least about 80% by weight water and a substantially water-insoluble, water-swellable, hydrophilic polymer; and
(b) at least one flexible composite scrim comprising a laminate of at least one foil or sheet of a metallic component selected from the group consisting of aluminum, copper, gold, silver, and brass and at least one film of a hydrophobic polymeric substrate, said scrim being in intimate contact with said flexible solid sheet and which metallic component has a sufficient thickness,
to provide a protective drape having top and bottom external surfaces, which drape is capable of effectively dissipating thermal energy associated with an accidentally directed beam of laser light.

50. A protective drape comprising:
(a) at least one flexible solid sheet comprising a porous polymer foam; and (b) at least one flexible composite scrim comprising a laminate of at least one foil or sheet of a metallic component selected from the group consisting of aluminum, copper, gold, silver, and brass and at least one film of a hydrophobic polymeric substrate, said scrim being in intimate contact with said foam and which metallic component has a sufficient thickness, to provide a protective drape having top and bottom external surfaces, which drape upon wet up by swelling the foam is capable of effectively dissipating thermal energy associated with an accidentally directed beam of laser light.

51. The protective drape of claim 1 in which said homogeneous mixture is at least about 90% by weight water.

52. The protective drape of claim 1 which is electroconductive.

53. A method of shielding an object from harmful optical radiation, electrical discharge, heat, or flame which comprises interposing at least one protective drape between the source of said harmful optical radiation, electrical discharge, heat, or flame and said object, said protective drape being in intimate contact with said object and which drape comprises:

(a) at least one flexible solid sheet of a viscoelastic hydrophilic gel comprising a homogeneous mixture of at least about 80% by weight water and a substantially water-insoluble, water-swellable, hydrophilic polymer; and (b) at least one flexible composite scrim comprising a laminate of at least one foil or sheet of a metallic component and at least one film of a hydrophobic polymeric substrate, said scrim being in intimate contact with said flexible solid sheet and which metallic component has a sufficient degree of reflectivity, thermal conductivity, and thickness, to provide a protective drape which is capable of effectively dissipating said harmful optical radiation, electrical discharge, heat, or flame which has accidentally been directed toward said object.

54. A method of shielding an object from harmful optical radiation, electrical discharge, heat, or flame which comprises interposing at least one protective drape between the source of said harmful optical radiation, electrical discharge, heat, or flame and said object, said protective drape being in intimate contact with said object and which drape comprises:

(a) at least one flexible solid sheet comprising a porous polymer foam; and (b) at least one flexible composite scrim comprising a laminate of at least one foil or sheet of a metallic component and at least one film of a hydrophobic polymeric substrate, said scrim being in intimate contact with said foam and which metallic component has a sufficient degree of reflectivity, thermal conductivity, and thickness, to provide a protective drape which upon wet up by swelling the foam is capable of effectively dissipating said harmful optical radiation, electrical discharge, heat, or flame which has accidentally been directed toward said object.

55. A method for retarding the ignition of a combustible material due to exposure to nonfocused laser light which comprises interposing at least one protective drape between the source of said nonfocused laser light and said combustible material, said protective drape being in intimate contact with said combustible material and which protective drape comprises:

(a) at least one flexible solid sheet of a viscoelastic hydrophilic gel comprising a homogeneous mixture of at least about 80% by weight water and a substantially water-insoluble, water-swellable, hydrophilic polymer; and (b) at least one flexible composite scrim comprising a laminate of at least one foil or sheet of a metallic component and at least one film of a hydrophobic polymeric substrate, said scrim being in intimate contact with said flexible solid sheet and which metallic component has a sufficient degree of reflectivity, thermal conductivity, and thickness, to provide a protective drape which is capable of effectively dissipating thermal energy associated with exposure to nonfocused laser light.

56. The method of claim 55 in which said viscoelastic hydrophilic gel comprises a mixture of at least about 90% by weight water and a substantially water-insoluble, water-swellable hydrophilic polymer.

* * * * *